United States Patent [19]

Kawashima et al.

[11] Patent Number: 4,932,242

[45] Date of Patent: Jun. 12, 1990

[54] CAPILLARY TYPE VISCOSIMETER

[75] Inventors: Sumihiko Kawashima, Ohtsu; Zenichiro Shirahama; Hidekazu Nakano, both of Tsuruga, all of Japan

[73] Assignee: Toyo Boseki Kabushiki Kaisha, Osaka, Japan

[21] Appl. No.: 182,143

[22] Filed: Apr. 15, 1988

[30] Foreign Application Priority Data

Apr. 17, 1987 [JP] Japan ................................ 62-96071
Sep. 3, 1987 [JP] Japan ................................ 62-221628

[51] Int. Cl.⁵ .......................................... G01N 11/08
[52] U.S. Cl. ....................................................... 73/55
[58] Field of Search .............................. 73/54, 55, 56

[56] References Cited

U.S. PATENT DOCUMENTS

| | | | |
|---|---|---|---|
| 3,435,665 | 4/1969 | Tzentis | 73/55 |
| 3,535,917 | 10/1970 | Blair et al. | 73/55 |
| 3,548,638 | 12/1970 | Mitsuo-Uchida et al. | 73/55 |
| 3,930,402 | 1/1986 | Detmar et al. | 73/55 |
| 4,143,541 | 3/1979 | Ito et al. | 73/55 |
| 4,213,747 | 7/1980 | Friedrich | 73/55 |
| 4,425,790 | 1/1984 | Bice et al. | 73/55 |
| 4,817,416 | 4/1989 | Blanch et al. | 73/55 |

FOREIGN PATENT DOCUMENTS

| | | | |
|---|---|---|---|
| 24559 | 12/1970 | Japan | 73/55 |
| 93633 | 4/1987 | Japan | 73/55 |
| 623051 | 8/1978 | U.S.S.R. | 73/55 |

Primary Examiner—Hezron E. Williams
Attorney, Agent, or Firm—Wegner & Bretschneider

[57] ABSTRACT

In a capillary viscosimeter, there are provided
a high pressure receiving chamber coupled to a predetermined point of a capillary with an inlet port to which the fluid to be measured is supplied,
a low pressure receiving chamber coupled to another predetermined point of the capillary,
a constant volume pump provided after the low pressure receiving chamber for removing fluid from the capillary, and
a fluid path coupled to the high pressure receiving chamber for by-passing the remainder of fluid which is not removed by the constant volume pump.

13 Claims, 7 Drawing Sheets

CAPILLARY TYPE VISCOSIMETER

BACKGROUND OF THE INVENTION

1. Field of the Invention

The present invention relates to a capillary type viscosimeter, and more particularly to a viscosimeter using a pressure difference between two points in a fine tube through which a fluid flows.

2. Description of the Prior Art

A continuous capillary viscosimeter is used for measuring viscosity of fluid continuously based on either a pressure difference between two points of a capillary through which the fluid supplied from a constant volume pump flows and an amount of the fluid flowing in the capillary under the Hagen Poseuille Law.

In the conventional viscosimeters of the above type, as shown in FIG. 1, fluid flow is taken in an inlet port 1 by a constant volume pump 3. All of the fluid flowing into a high pressure chamber 4 is taken in a capillary 5. The fluid flows to a chamber 6 and in turn an outlet 2. A differential pressure sensor 8 is connected to the chambers 4 and 6 through pipes 7.

In order to measure the viscosity using the Hagen Poseuille Law, it is desired that the fluid flowing the capillary 5 is a laminated flow. Therefore, the discharge of the constant volume pump 3 should not be large and it takes time to flow from the inlet 1 of the measuring fluid to the inlet of the capillary 5. Particularly, when a pressure diaphragm is provided for taking out the pressure difference, since the diameter of the diaphragm is 90 mm, a long measurement time is needed.

Besides, in order to measure the viscosity of fluid of low viscosity with a high accuracy, the capillary must be long. In case of using a straight capillary, the capillary must be very long and the viscosimeter becomes bulky. In order to avoid the inconvenience, it has been proposed to form the capillary in a spiral shape.

According to the conventional measurement of the viscosity, viscosity $\mu$ can be calculated by the equation (1).

$$\mu = \frac{\pi r_4 \Delta P}{8(l + nr)q} - \frac{m \rho q}{8 \pi(l + nr)} \quad (1)$$

wherein
l: length of the capillary,
r: radius of the capillary
$\rho$: density of the fluid to be measured
n: tube end correction factor of the capillary
m: kinetic energy factor Normally, the viscosimeter is so designed that $$\frac{\pi r^4 \cdot \Delta P}{8(l + nr)q} >> \frac{m \cdot \rho \cdot q}{8\pi(l + nr)} \quad (2)$$

so as to make the relation between $\Delta P$ and $\mu$.
Then the equation (1) can be expressed as 0107

$$\mu \approx \frac{\pi r^4 \Delta P}{8(l + nr)q} \quad (3)$$

A problem of the conventional measurement of viscosity using the above equation (3) is in that the accuracy of the measurement becomes low in the low viscosity region due to the fact that the accuracy of the differential pressure sensor is affected by the valve of the measured pressure difference relative to the full scale value of the available measurement range. Thus, the accuracy becomes poor in the low viscosity region.

Since the accuracy of the differential pressure sensor directly affects the accuracy of the measurement result of the viscosity, it is difficult to obtain a measurement result whose accuracy is higher than the accuracy of the pressure difference sensor.

SUMMARY OF THE INVENTION

An essential object of the present invention is to provide a viscosimeter of a high response speed.

Another object of the present invention is to provide a viscosimeter which is able to measure the viscosity from very low viscosity to very high viscosity with a high accuracy.

A further object of the present invention is to provide a viscosimeter which is able to measure viscosity with a high accuracy without regard to the accuracy of a pressure difference sensor.

According to the present invention, there is provided a capillary viscosimeter comprising a capillary having its one end connected to a high pressure receiving chamber with another end connected to a low pressure receiving chamber, a fluid path connected to said high pressure receiving chamber for bypassing a part of the fluid flowing into said high pressure receiving chamber and a constant volume pump coupled to said low pressure receiving chamber.

The capillary may be any type of a pipe, such as a straight pipe, a vortex shaped pipe, spiral pipe or zigzag shaped pipe. However, in order to measure the viscosity of low viscosity fluid, the vortex shaped pipe, spiral pipe or zigzag shaped pipe are suitable.

The provision of the fluid path enables the supply of a large amount of the fluid from an inlet to the high pressure receiving chamber and it is possible to provide the inlet of the capillary near the inlet of the high pressure receiving chamber, whereby the delay of the measuring time of the viscosimeter can be eliminated.

When the capillary is a vertex shape, since the length of the capillary may be increased without increasing the size of the viscosimeter, it becomes possible to measure the viscosity of the low viscosity fluid with a high accuracy.

When the capillary is a vertex shaped pipe or spiral shaped pipe, there may occur an error $\epsilon$ due to a pressure loss of the fluid as shown in equation (4).

$$\epsilon = 1/48 \, (r/R)^2 \quad (4)$$

wherein r is the radius of the capillary and
R is the radius of curvature of the capillary.

Accordingly, by determining the values r and R as R>>r, it is possible to make the error $\epsilon$ negligibly small. For example, assuming that R=50 mm and r=2 mm, the error is $\epsilon$ = 0.000033
= 0.0033(%).

Since the allowable error of the continuous capillary viscosimeter is 1 to 3%, the error mentioned above may be neglected.

In order to measure the viscosity of fluid over a wide range of viscosity including low viscosity, the viscosimeter may comprise a constant volume pump for supplying fluid to be measured to said capillary, a pressure sensor for measuring a pressure difference between two points of said capillary, a control means for controlling the rotational speed of said pump so that the differential pressure between said two points of the capillary is constant, means for detecting the rotational speed of the pump and calculation means for calculating the viscosity of the fluid by the signal of the detecting means.

DETAILED DESCRIPTION OF THE INVENTION

Figure 1:
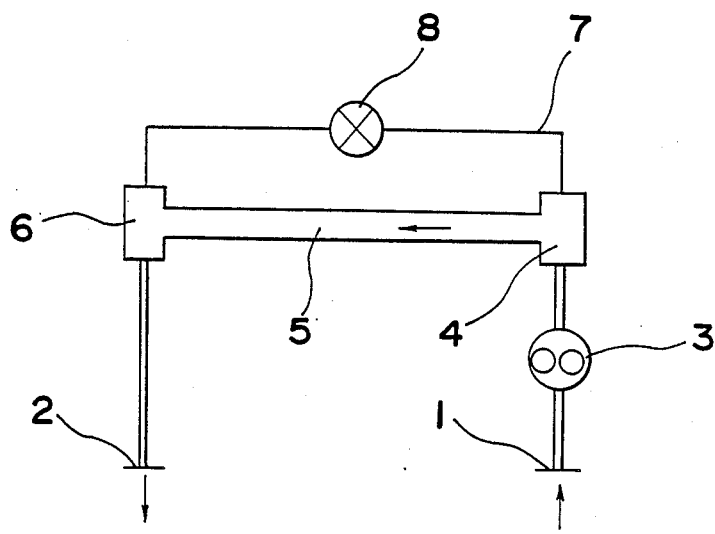
FIG. 1 is a schematic diagram showing a conventional capillary viscosimeter.

Before the description of the preferred embodiment of the viscosimeter according to the present invention proceeds, the principle of the measurement of the viscosimeter according to the present invention will be explained.

It is further noted that the same members are designated by the same reference numerals throughout the drawings.

Figure 12:
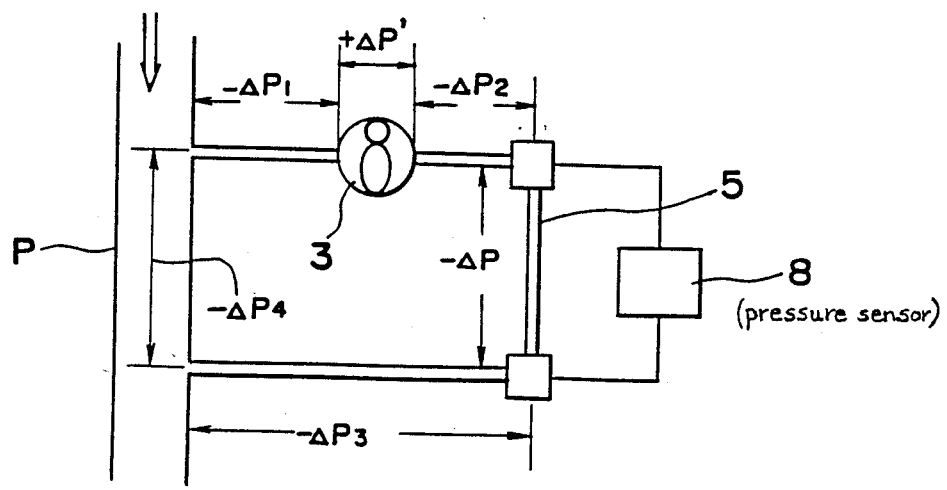
FIG. 12 is a schematic diagram showing general structure of the capillary viscosimeter according to the present invention.
Figure 7:
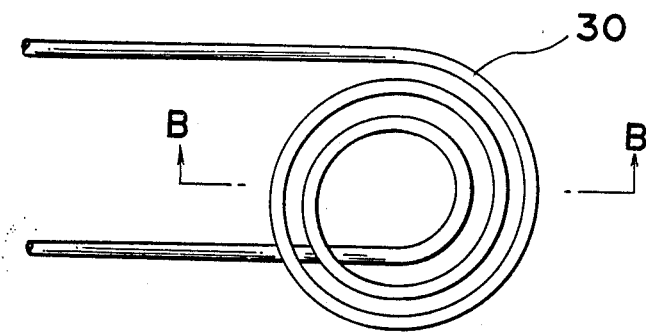
FIG. 7 is a plan view showing an example of the capillary used in the example shown in FIG. 6.
Figure 8:
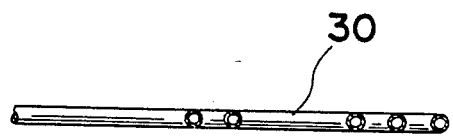
FIG. 8 is a cross sectional view taken along the lines B—B in FIG. 7.

Referring to FIG. 12, $\Delta P$, $\Delta P1$ to $\Delta P4$ and $\Delta P'$ denote respective differential pressures between respective two points. A gear pump 3 with highly accurate discharge is used for supplying the fluid to the capillary. The discharge of the gear pump 3 is expressed as the equation (5).

$$q = K_1 N - K_2(\Delta P'/\mu) \tag{5}$$

wherein
q: discharge (cc/min)
N: rotational speed of the pump (rpm)
$\Delta P'$: differential pressure between the inlet and outlet of the pump (kg/cm$^2$)
$\mu$: viscosity of the fluid (poise)
$K_1, K_2$: constant In the equation (5), $K_2 (\Delta P'/\mu)$ is a slip value.

In the capillary viscosimeter, as the value $\Delta P'$ is 0.1 to 0.5 kg/cm$^2$, $K_1 N >> K_2(\Delta P'/\mu)$. Since the value ($K_2 (\Delta P'/\mu))/K_2 N$ is a small value such as 0.0005, the slip value can be neglected. The slip value can also be eliminated in such a way as mentioned below.

The following equation can be obtained.

$$\Delta P' = \Delta P_1 + \Delta P_2 + \Delta P_3 + \Delta P - \Delta P_4 \tag{6}$$

By selecting the inlet and outlet of the capillary viscosimeter so as to obtain $$\Delta P_4 << (\Delta P_1 + \Delta P_2 + \Delta P_3 + \Delta P_3 + \Delta P),$$
the equation (6) may be changed to
$$\Delta P' \approx \Delta P_1 + \Delta P_2 + \Delta P_3 + \Delta P.$$

By selecting the diameter of the respective fluid paths in FIG. 12 so as to provide a laminar fluid flow, the following equation can be obtained from the equation 3.
$\Delta P_1 + \Delta P_2 + \Delta P_3 \approx q$ wherein k3 is a constant.
Accordingly, $\Delta P' \approx \Delta P + q\mu/K_3$ (7)
From the equation (3), $$\mu \approx \frac{\pi r^4}{8(l + nr)} \cdot \frac{\Delta P}{q} = K_4 \frac{\Delta P}{q} \tag{8}$$

is established.
From the equations (5), (7) and (8), $$q = \frac{K_1}{(K_2/K_3 + K_2/K_4 + 1)} N = KN \tag{9}$$

Therefore, by selecting the inlet position, outlet position of the capillary viscosimeter and the diameters of the paths so as to satisfying the equation (7), it is possible to eliminate the effect of the slip, whereby the rotation speed of the gear pump 3 is exactly proportional to the discharge from the gear pump 3.

According to the present invention, there is provided a control device for controlling the rotational speed of the gear pump so that the differential pressure between two points of the capillary is a predetermined constant value. In such a situation, the relation between the viscosity $\mu$ of the fluid and the rotation speed of the gear pump is expressed as $$\mu \approx K_4/K \times \Delta P/N \tag{10}$$

Therefore, the viscosity of the fluid can be obtained by measuring the rotational speed of the gear pump.

The rotational speed of the gear pump in a digital form by means of a rotary encoder or magnetic sensor with extremely high accuracy compared to the accuracy of the differential pressure sensor.

EXAMPLE 1

Figure 2:
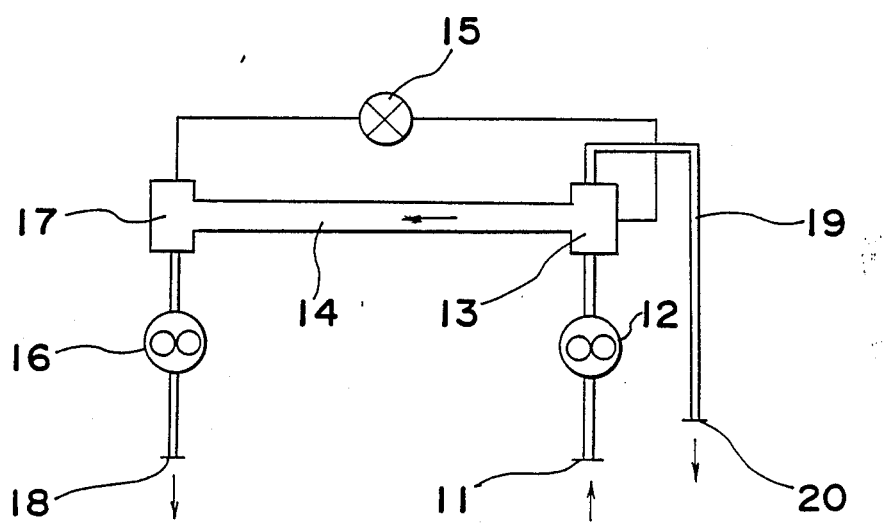
FIG. 2 is a schematic diagram showing an example of a capillary viscosimeter according to the present invention.

Referring to FIG. 2, the fluid to be measured is supplied to an inlet port 11 of a delivery pump 12, which delivers the fluid to a high pressure receiving chamber 13 connected to a capillary 14 and a differential pressure sensor 15. A part of the fluid in the high pressure receiving chamber 13, the volume of which is constant, is derived to the capillary 14 drawn by a constant volume pump 16 through a low pressure receiving chamber 17 and the fluid drawn by the constant volume pump 16 is exhausted through an exhausting port 18.

Excess fluid in the high pressure receiving chamber 13 is exhausted through a path 19 to an exhausting port 20.

The differential pressure sensor 15 is connected between the high pressure receiving chamber 13 and low pressure receiving chamber 17 for detecting the differential pressure therebetween.

In the arrangement mentioned above, the discharge of the delivery pump 12 is set greater than the discharge of the constant volume pump 16. As the discharge of the delivery pump 12 increases, the measurement time decreases.

In operation, the pump 12 feeds the fluid to be measured which is supplied to the inlet port 11, to the high pressure receiving chamber 13. A constant volume of the fluid in the high pressure receiving chamber 13 is drawn by the constant volume pump 16 through the capillary 14 and the low pressure receiving chamber 17. The pressure difference between both ends of the capillary 14 is measured by the differential pressure sensor 15, whereby the viscosity of the fluid can be measured by the volume of the fluid flowing the capillary 14, i.e., discharge of the constant volume pump 16 and the differential pressure measured by the differential pressure sensor 15 using the equation 10.

In the arrangement mentioned above, when there is a pressure high enough to supply the fluid to the high pressure receiving chamber 13 or there is provided a suitable pump upstream as the viscosimeter, the delivery pump 12 may be omitted.

Figure 3:
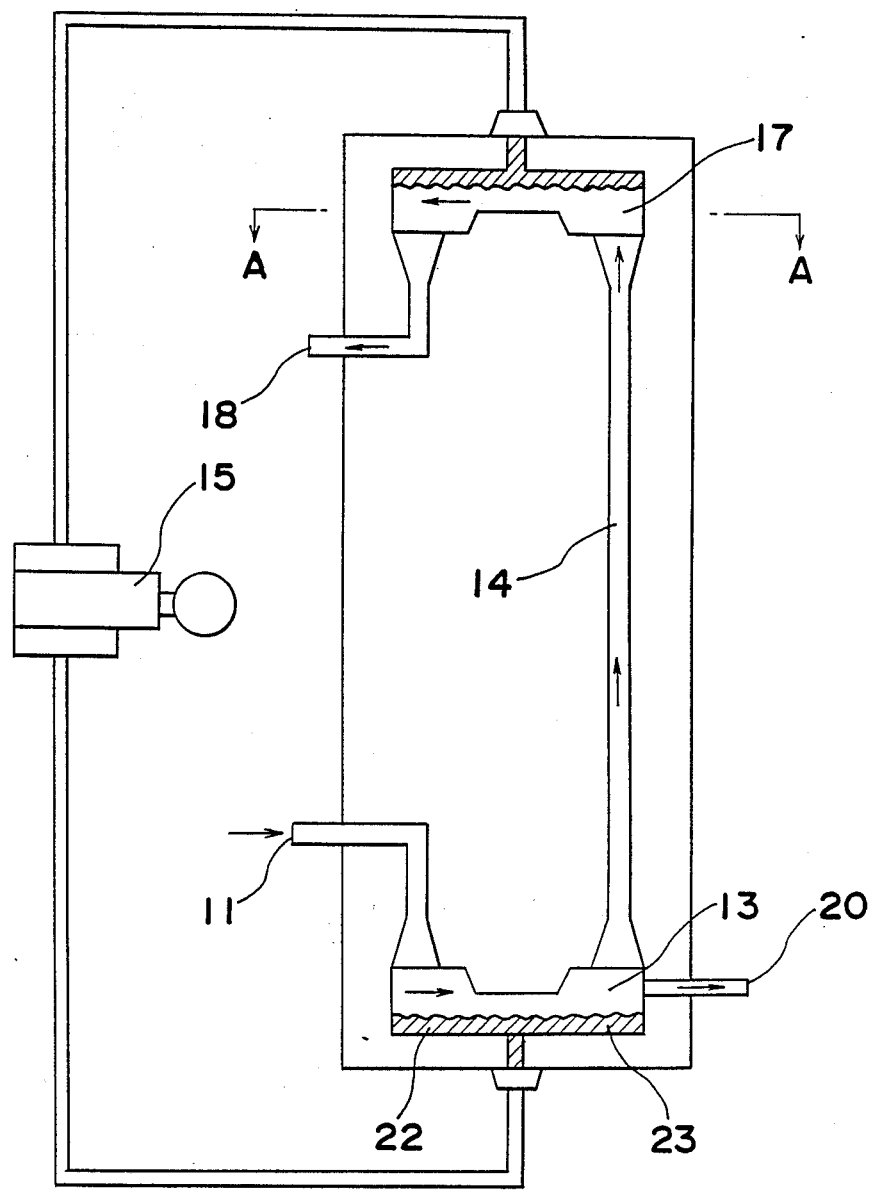
FIG. 3 is a schematic diagram showing an example of a pressure receiving chamber used in the capillary viscosimeter shown in FIG. 2.
Figure 4:
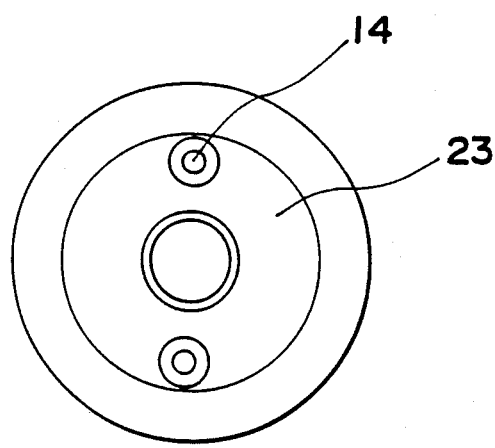
FIG. 4 is a cross sectional view taken along the lines A—A in FIG. 3, FIG. 5A and FIG. 5B are respectively schematic diagrams showing examples of a capillary viscosimeter according to the present invention.

A specific example of both the pressure receiving chambers 13 and 17 is shown in FIG. 3, wherein a seal diaphragm differential pressure sensor is used. The seal diaphragm differential pressure sensor transmits the pressure received through the reception diaphragm 23 to the differential pressure sensor 15 through seal liquid 22. This system is usually used in an arrangement for the measurement of a high temperature fluid. The diameter of the reception diaphragm 23 is about 90 mm and the volume of the high pressure receiving chamber 13 the becomes large. Therefore, a conventional viscosimeter using the seal diaphragm differential pressure sensor has a drawback in that there is a long delay time for measuring the viscosity of the fluid. However, the viscosimeter having the bypass line 19 in the high pressure receiving chamber 13 can eliminate this drawback of the delay time for the measurement as mentioned above, since a great amount of the fluid can be supplied to the high pressure receiving chamber 13.

EXAMPLE 2

Figure 5A:
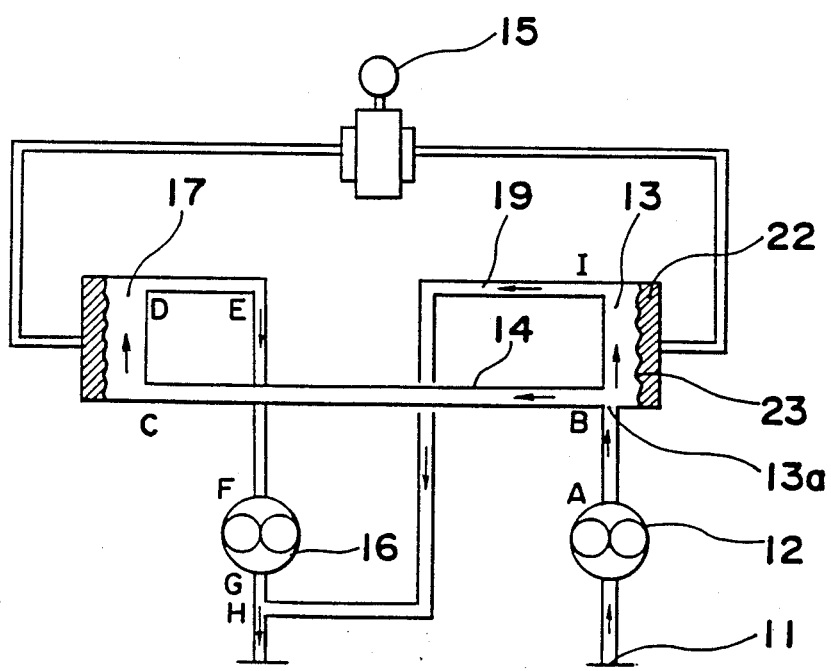

Referring to FIG. 5A, one end of the capillary 14 is coupled to the high pressure receiving chamber 13 at a position near the inlet port 13a to which the fluid is supplied from the delivery pump 12. In this arrangement, the fluid entering in the high pressure receiving chamber 13 can flow in the capillary 14 directly. Therefore, it is possible to eliminate the effect of the time delay due to holding of the fluid in the high pressure receiving chamber 13, thereby resulting in improving the speed of the measurement of the viscosity. It is assumed that the pressure drop between the output port of the delivery pump 12 and input port of the constant volume pump 16 through the capillary 14, indicated by path A, B, C, D, E and F, is $\Delta P_1$, the pressure drop between the outlet port G of the constant volume pump 16 and a connecting point H of the path 19 is $\Delta P_2$ and the pressure drop between the points A and H through the points B and I is $\Delta P_3$. When the arrangement shown in FIG. 5 is set to satisfy the equation $$\Delta P_1 + \Delta P_2 = \Delta P_3 \qquad (11)$$

it is possible to make the differential pressure between the inlet port and outlet port of the constant volume pump 16 zero, whereby it is possible to neglect the error of the fluid flow volume of the constant volume pump resulting in improving the accuracy of the measurement.

When the discharge of the delivery pump 12 is twice of that of the constant volume pump 16, the volume of the fluid passing through the high pressure receiving chamber 13 is equal to the volume of the fluid passing through the low pressure receiving chamber 17, the pressure drops occurring in both chambers 13 and 17 are equal. Accordingly, the effect occurring in both chambers 13 and 17 can be offset. Thus the differential pressure sensor 15 measures an exact pressure drop in the capillary 14, so that the error due to the seal diaphragm arrangement can be eliminated.

Figure 5B:
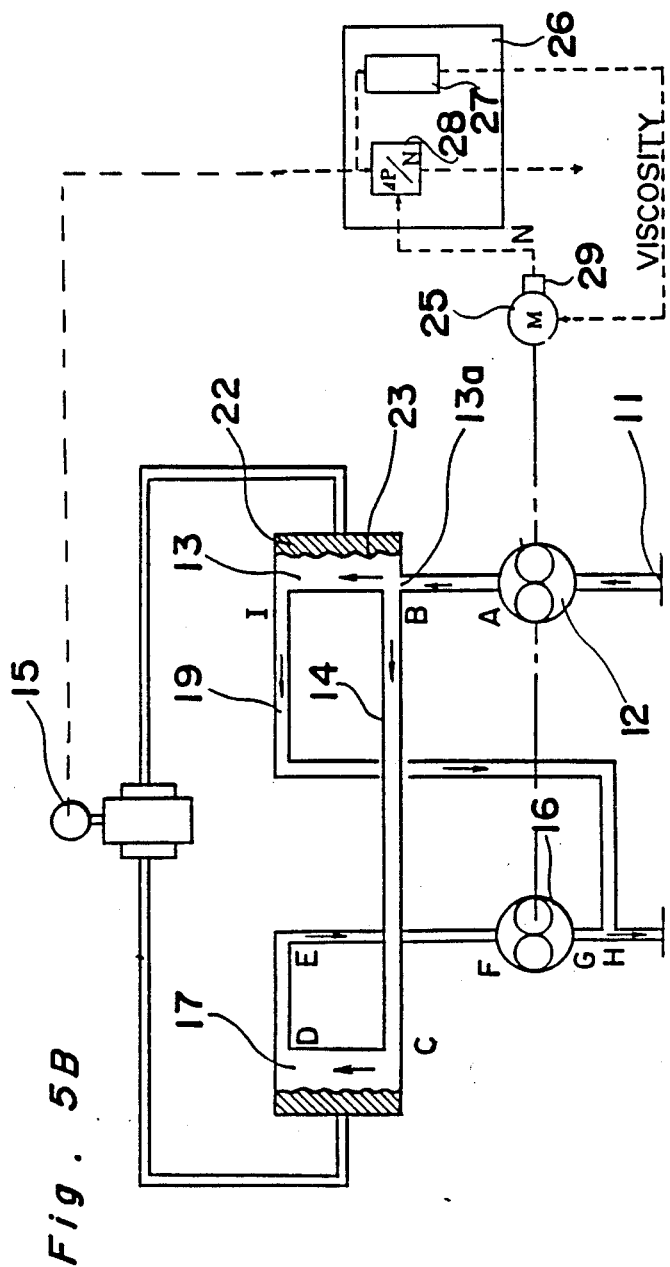

Referring to FIG. 5B showing a modification of the example shown in FIG. 5A, the pumps 12 and 16 are driven by a servo motor 25 so that the flow amount of the constant volume pump (for delivering fluid to the capillary) 12 is twice the flow amount of the measuring pump 16 of constant volume type. A control unit 26 including a microcomputer is provided for controlling the servo motor 25. The control unit 26 receives the output signal of the differential pressure sensor 15 at a servo control circuit 27 and viscosity calculation circuit 28.

The measuring fluid taken by the pump 12 is supplied to the bypass line 19 and capillary 14. The flow amount q of the capillary 14 is decided by the flow amount of the pump 16 and the flow amount is expressed by the equation (3) in which n=0. Assuming that the rotation speed of the pump 16 to be N and the flow amount of the pump 16 per one rotation to be C, following equation can be obtained.

$$q = NC$$

Thus, the equation (1) can be rewritten as $$\mu = \frac{\pi r^4 \cdot \Delta P}{8 \cdot (l + nr) \cdot C} \cdot \frac{1}{N}$$

The differential pressure between the input and output of the capillary 14 is measured by the differential pressure sensor 15 and the measurement result is transferred to the respective circuits 27 and 28. The control unit 26 controls the servo motor 25 so that the differential pressure is constant by controlling the speed of the servo motor 25. The rotation speed N of the servo motor 25 is sensed by a resolver 29 and the speed N is applied to the circuit 28 to calculate $\Delta P/N$, whereby the viscosity $\mu$ can be calculated by the equation mentioned above. In this arrangement, there may occur an offset $\pm 0.1\%$ of the differential pressure. In order to eliminate the measurement error due to the offset, the differential pressure is divided by the rotation speed to eliminate the effect of the servo control error.

EXAMPLE 3

Figure 6:
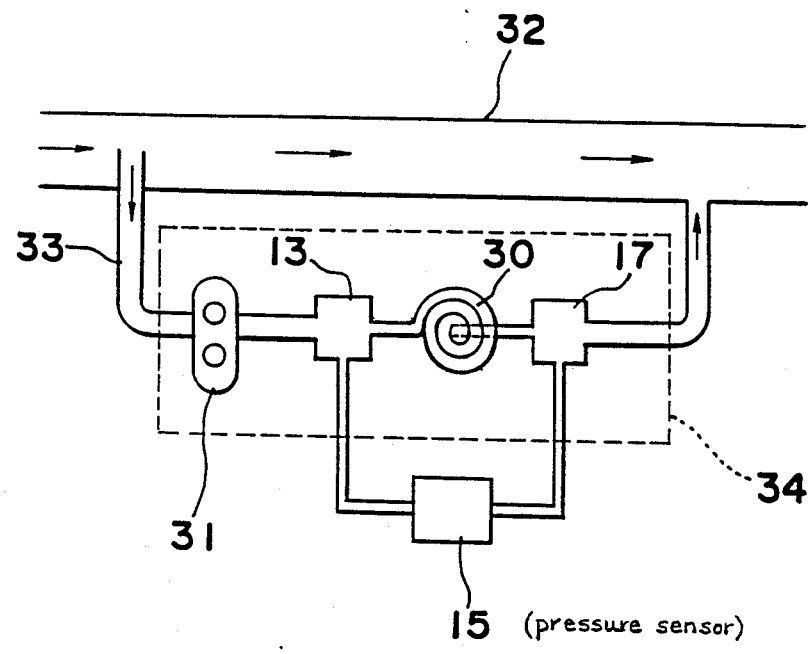
FIG. 6 is a schematic diagram showing an example of a capillary viscosimeter according to the present invention.

Referring to FIG. 6, there is provided a capillary 30 in a spiral shape with its one end connected to the high pressure receiving chamber 13 and another end connected to the low pressure receiving chamber 17. The high pressure receiving chamber 13 is adapted to receive the fluid to be measured from a constant volume pump 31 coupled to a fluid path 32 through an inlet path 33. The low pressure receiving chamber 17 is coupled to the fluid path 32 through an outlet path at a downstream position relative to the position where the inlet path 33 is coupled to the fluid path 32. The differential pressure sensor 15 is connected to both of the chambers 13 and 17. The viscosimeter mentioned above is accommodated in a constant temperature bath 34. The principle of the measurement of the viscosity in the arrangement shown in FIG. 6 is the same as that of the conventional viscosimeter. Namely, the constant volume pump 31 takes the fluid from the fluid path 32 and feeds it to the capillary 30. The fluid passing the capillary 30 flows in the fluid path 32. The pressure difference between the high pressure receiving chamber 13 and low pressure receiving chamber 17 is measured by the differential pressure sensor 15.

In the arrangement in the example 3, it is possible to extend the length of the capillary 30 within a small space.

Various modifications of the capillary 30 are shown in FIGS. 7 to 10. In the example shown in FIG. 7, the capillary is formed in a spiral shape in substantially the same plane.

Figure 9:
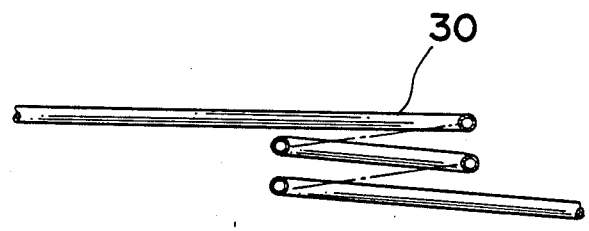
FIG. 9 is a side view showing another example of a capillary used in the capillary viscosimeter shown in FIG. 6.

In the example shown in FIG. 9, the capillary is formed in a helical shape having each coil formed with a similar diameter.

Figure 10:
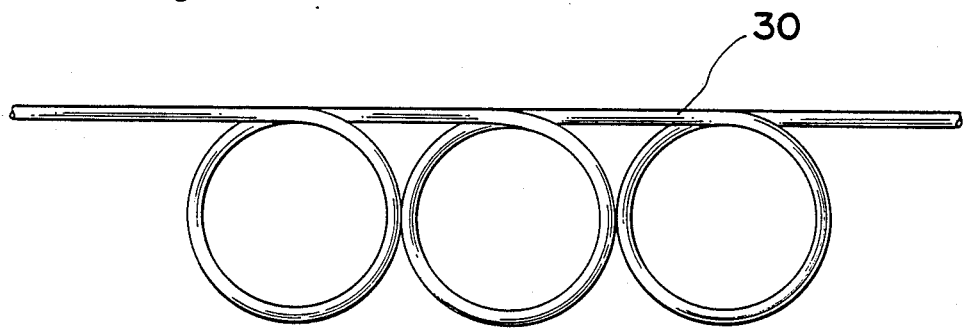
FIG. 10 is a plan view showing a further example of a capillary used in the example shown in FIG. 6.

In the example shown in FIG. 10, a plurality of single turn coils are formed with the centers of the coils displaced in the direction of the axis of the capillary. The shape of the coil of the capillary may be changed as desired so far as the size of the capillary can be decreased.

EXAMPLE 4

Figure 11:
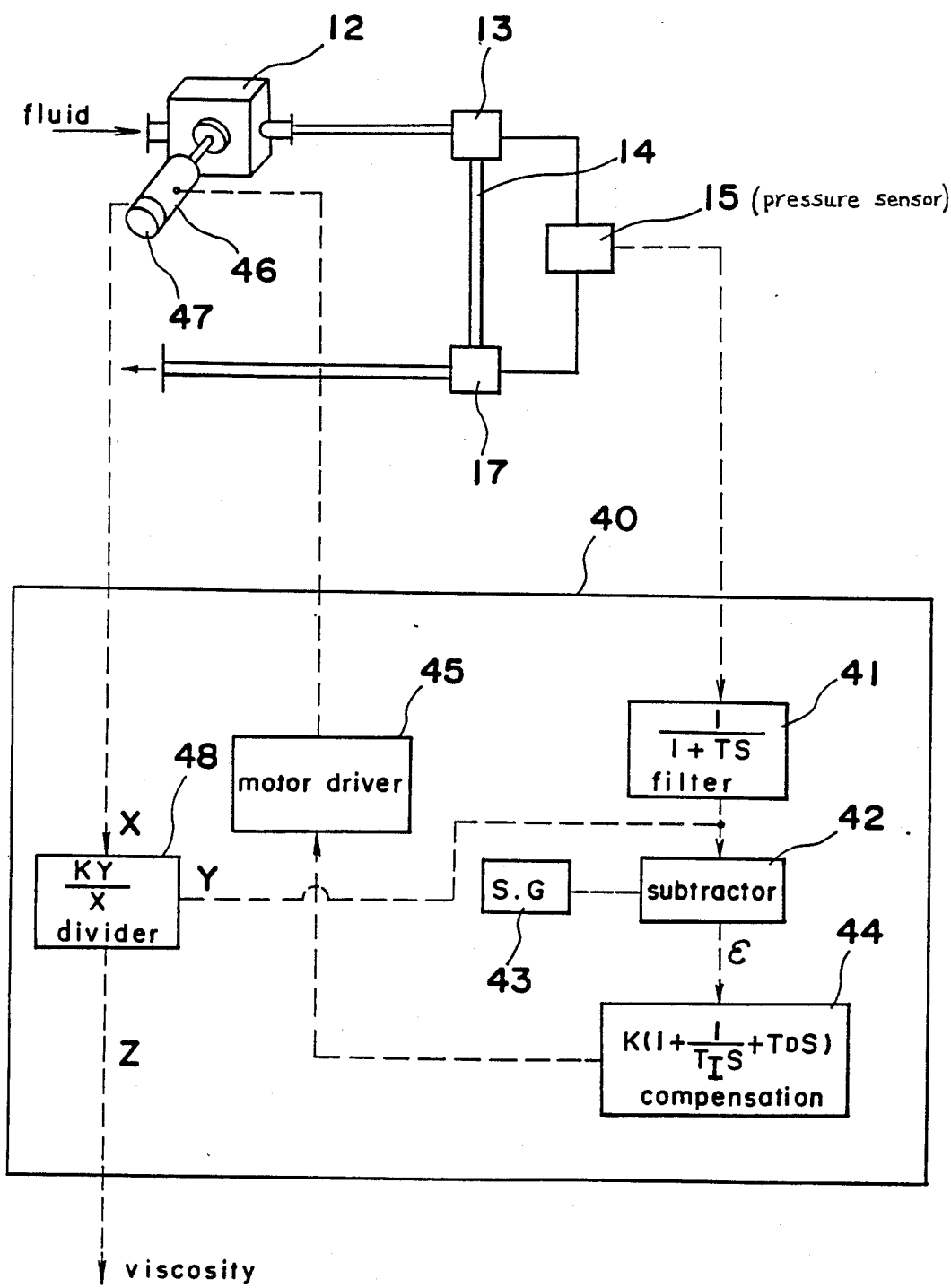
FIG. 11 is a block diagram showing a calculation unit used in the capillary viscosimeter according to the present invention.

Shows FIG. 11 showing a further example of the viscosimeter according to the present invention in which a calculation device 40 is provided for calculating the viscosity of the fluid. The output of the differential pressure sensor 15 is applied to a filter 41 for filtering a noise component of the output signal of the differential pressure sensor 15. The output signal of the filter 41 is applied to a subtractor 42 which receives a standard signal from a signal generator 43. The subtractor 42 calculated the difference between the output signal of the filter (referred to as the pressure difference signal) and the standard signal and generates a differential signal, which is applied to a compensation circuit 44 including P I D controller. The output of the compensation circuit 44 is applied to a motor driver circuit 45 for controlling the rotational speed of an electric motor 46 for driving the delivery pump 12. A speed sensor 47 is provided on the motor 46 for detecting the rotational speed of the delivery pump 12. The output signal of the speed sensor representing the speed (the amount of which is presented by X) of the delivery pump 12 is applied to a divider circuit 48 to which the pressure difference signal (the amount of which is represented by Y) is applied so that a calculation $K^1 (X/Y)$, wherein $K^1$ is a constant, is performed and outputs the viscosity (which is represented by Z) of the fluid. In the arrangement shown in FIG. 11, when the differential signal $\epsilon$ is outputted from the subtractor 42, the compensation circuit 44 calculates $$K\epsilon + \frac{1}{T_I} \int \epsilon \, dt + T_D \frac{d\epsilon}{dt}$$

where $K$, $T_I$ and $T_D$ are constants.

The result of the above calculation is applied to the motor driver circuit 45 in which the signal is amplified so that the signal can drive the motor 46. The motor 46 and the delivery pump 12 are rotated at a speed. The speed of the motor 46 is controlled by the signal of the compensation circuit so that the differential value $\epsilon$ is zero. The speed of the motor 46 is detected by the sensor 47 and the speed signal having the value X is applied to the divider circuit 48 to calculate $K^1 \cdot (X/Y)$ representing the viscosity of the fluid. As the speed sensor 47, a rotary encoder may be used for obtaining the signal in digital form.

In the various examples mentioned above, the inner diameter of the capillary may be 1 to 15 mm.

It is noted that the various kinds of the capillary shown in FIGS. 6 to 10 can be employed as the capillary in the embodiments shown in FIGS. 2, 5A, 5B and 11.

What is claimed is:

1. A capillary viscosimeter, comprising:
   a capillary having upstream and downstream ends;
   a delivery pump for supplying fluid to be measured to the upstream end of the capillary;
   a constant volume pump for removing fluid from the downstream end of the capillary;
   a high pressure chamber at the upstream end of the capillary, which receives fluid from the delivery pump;
   a low pressure chamber at the downstream end of the capillary, from which the constant volume pump removes fluid;
   a fluid bypass path communicating with the high pressure chamber, for carrying fluid not removed by the constant volume pump;
   pressure detecting means for detecting a pressure difference between two points of the capillary;
   pump control means for controlling the speed of at least the constant volume pump so that the pressure difference remains substantially constant;
   speed detecting means for detecting the speed of the constant volume pump; and
   means for calculating the viscosity of the fluid through the speed detected by the speed detecting means.

2. The viscosimeter of claim 1, wherein the bypass path is in communication with a line downstream of the constant volume pump so that fluid is carried by the bypass path from the high pressure chamber to the line downstream of the constant volume pump.

3. The viscosimeter of claim 2, wherein the pump control means comprises a servo motor which controls the speed of the delivery pump and the constant volume pump.

4. The viscosimeter of claim 1, wherein the upstream end of the capillary is connected to the high pressure chamber near an inlet for the high pressure chamber which receives fluid from the delivery pump.

5. The viscosimeter of claim 1, wherein the pressure detecting means is in communication with the high pressure chamber and the low pressure chamber.

6. The viscosimeter of claim 1, wherein the capillary has a shape selected from the group consisting of straight, spiral, helical and zigzag.

7. The viscosimeter of claim 6, wherein the capillary has an inner diameter of 1 to 15 mm.

8. A capillary viscosimeter, comprising:
a capillary having upstream and downstream ends;
a high pressure chamber at the upstream end of the capillary;
a low pressure chamber at the downstream end of the capillary;
a delivery pump for supplying fluid to be measured to the high pressure chamber;
a constant volume pump for removing fluid from the low pressure chamber;
a fluid bypass path communicating with the high pressure chamber and a line downstream of the constant volume pump, for carrying fluid not removed by the constant volume pump from the high pressure chamber to the line downstream of the constant volume pump;
pressure detecting means for detecting a pressure difference between two points of the capillary;
pump control means for controlling the speed of the delivery pump and the constant volume pump so that the pressure difference remains substantially constant;
speed detecting means for detecting the speed of the constant volume pump; and
means for calculating the viscosity of the fluid through the speed detected by the speed detecting means.

9. The viscosimeter of claim 8, wherein the pump control means comprises a servo motor which controls the speed of the delivery pump and the constant volume pump.

10. The viscosimeter of claim 8, wherein the upstream end of the capillary is connected to the high pressure chamber near an inlet for the high pressure chamber which receives fluid from the delivery pump.

11. The viscosimeter of claim 8, wherein the pressure detecting means is in communication with the high pressure chamber and the low pressure chamber.

12. The viscosimeter of claim 9, wherein the speed detecting means detects the rotation speed of the servo motor.

13. The viscosimeter of claim 9, wherein the servo motor controls the delivery pump and the constant volume pump so that the fluid delivered by the delivery pump is twice that removed by the constant volume pump.

* * * * *